(12) United States Patent
    Olaf

(10) Patent No.: US 10,391,230 B2
(45) Date of Patent: Aug. 27, 2019

(54) CANNULA DEVICE, ARTIFICIAL LUNG

(71) Applicant: CENTRE CHIRURGICAL MARIE LANNELONGUE, Le Plessis Robinson (FR)

(72) Inventor: Mercier Olaf, Fontenay aux roses (FR)

(73) Assignee: CENTRE CHIRURGICAL MARIE LANNELONGUE, Le Plessis Robinson (FR)

( * ) Notice: Subject to any disclaimer, the term of this patent is extended or adjusted under 35 U.S.C. 154(b) by 35 days.

(21) Appl. No.: 15/565,295

(22) PCT Filed: Apr. 8, 2016

(86) PCT No.: PCT/EP2016/057857
§ 371 (c)(1),
(2) Date: Oct. 23, 2017

(87) PCT Pub. No.: WO2016/162543
PCT Pub. Date: Oct. 13, 2016

(65) Prior Publication Data
US 2018/0078698 A1    Mar. 22, 2018

(30) Foreign Application Priority Data
Apr. 9, 2015  (FR) ...................... 15 53080

(51) Int. Cl.
*A61M 1/36* (2006.01)
*A61M 1/16* (2006.01)
(Continued)

(52) U.S. Cl.
CPC ........ *A61M 1/3659* (2014.02); *A61M 1/1698* (2013.01); *A61M 1/3666* (2013.01);
(Continued)

(58) Field of Classification Search
CPC .............. A61M 1/3659; A61M 1/3667; A61M 1/3666; A61M 25/003; A61M 25/04;
(Continued)

(56) References Cited

U.S. PATENT DOCUMENTS

2008/0200877 A1* 8/2008 Panotopoulos ..... A61M 1/0058
                                                    604/131
2011/0282195 A1   11/2011 Solar et al.
(Continued)

FOREIGN PATENT DOCUMENTS

WO    WO 2015/009904 A1    1/2015

OTHER PUBLICATIONS

International Search Report as issued in International Patent Application No. PCT/EP2016/057857, dated Jul. 15, 2016.

*Primary Examiner* — Philip R Wiest
(74) *Attorney, Agent, or Firm* — Pillsbury Winthrop Shaw Pittman LLP

(57) ABSTRACT

A cannula device for the circulation of the blood in an artificial lung, includes: an aspiration lumen including at least one orifice permitting the aspiration of a volume of blood; an injection lumen including at least one orifice permitting the injection of a volume of blood, wherein the injection lumen and the aspiration lumen are held rigidly connected over at least a portion of their length, the lumens being sealed in relation to each other, the injection lumen having a deformable element, which is held on a portion of the distal end thereof, the deformable element having a first setting and a second setting, the change from the first setting to the second setting being effected by a modification of the diameter of the deformable element.

19 Claims, 12 Drawing Sheets

(51) Int. Cl.
*A61M 25/00* (2006.01)
*A61M 25/04* (2006.01)
(52) U.S. Cl.
CPC ........ *A61M 1/3667* (2014.02); *A61M 25/003* (2013.01); *A61M 25/04* (2013.01); *A61M 2025/0031* (2013.01); *A61M 2205/0266* (2013.01); *A61M 2205/36* (2013.01)
(58) Field of Classification Search
CPC .. A61M 2025/0031; A61M 2205/0266; A61M 2205/36
See application file for complete search history.

(56) References Cited

U.S. PATENT DOCUMENTS

| | | | | |
|---|---|---|---|---|
| 2012/0289895 | A1* | 11/2012 | Tsoukalis | A61M 25/0075 604/35 |
| 2012/0302995 | A1 | 11/2012 | Hochareon | |
| 2014/0012066 | A1 | 1/2014 | Aboul-Hosn et al. | |
| 2015/0224284 | A1* | 8/2015 | Panotopoulos | A61M 25/0026 604/43 |

* cited by examiner ized in that the injection lumen and the aspiration lumen are held rigidly connected over at least a portion of their length, said lumens being sealed in relation to each other, the injection lumen comprising a deformable element held over a portion of the distal end thereof, said deformable element comprising a first setting called "pass" and a second setting called "hold", the change from the first setting to the second setting being effected by a modification of the diameter of said deformable element.

CANNULA DEVICE, ARTIFICIAL LUNG

CROSS-REFERENCE TO RELATED APPLICATION

This is the U.S. National Stage of PCT/EP2016/057857, filed Apr. 8, 2016, which in turn claims priority to French Patent Application No. 1553080, filed Apr. 9, 2015, the entire contents of all applications are incorporated herein by reference in their entireties.

TECHNICAL FIELD OF THE INVENTION

The present invention relates to a cannula device for the circulation of blood in an artificial lung and to an artificial lung comprising said cannula device.

The invention finds particularly interesting application for putting in place an artificial lung intended to be used by a patient for a long time.

TECHNOLOGICAL BACKGROUND OF THE INVENTION

Cannulas currently exist making it possible to offer an artificial lung solution. These cannulas enable a circulation of the blood in a closed circuit thanks to a technique for oxygenating a volume of blood low in oxygen taken from a body.

Such cannulas are currently used, for example, with an artificial lung system of ECMO type, designating "Extracorporeal Membrane Oxygenation". Such a system makes it possible to offer a solution for oxygenating a volume of blood taken from a patient and circulating through cannulas by means of a membrane.

A first solution consists in using a pair of cannulas which is introduced via the veins of a patient. The circuit thereby formed is named VV because it is formed by veno-venous route. In this case, the circulation of the blood occurs through the veins.

A second solution consists in using a pair of cannulas, one of which is introduced by venous route and the other by arterial route. This circuit is called AV because it is carried out by arterio-venous route. To do so, specific cannulas are adapted to the flow of blood to withdraw and to inject. The terms arterial cannula and venous cannula are commonly employed.

In both cases, the blood extracted from the venous system is oxygenated outside the body. In the VA ECMO, the blood thereby re-oxygenated is returned to recirculation through the arterial system, whereas in the VV ECMO, the operation takes place through the venous system.

A drawback of the first solution is the limitation of the cardiac and pulmonary assistance of a patient in oxygenated blood. The practical advantage of introducing the cannulas by venous routes finds a limitation in the efficiency of transporting oxygenated blood into certain organs.

A drawback of the second solution is the difficulty of putting in place and holding an injection cannula in an artery. Notably, this technique imposes a reduced mobility of the patient because the flow of blood to inject and the movements of the blood fluid can perturb the putting in place of a cannula and make its holding in place unstable.

SUMMARY OF THE INVENTION

An object of the invention relates to a cannula device for the circulation of a fluid in an artificial lung characterized in that it comprises:

a first lumen, called the aspiration lumen, comprising at least one orifice permitting the aspiration of a volume of the fluid, a second lumen, called the injection lumen, comprising at least one orifice permitting the injection of a volume of the fluid, characterized in that the injection lumen and the aspiration lumen are held rigidly connected over at least a portion of their length, said lumens being sealed in relation to each other, the injection lumen comprising a deformable element held over a portion of the distal end thereof, said deformable element comprising a first setting called "pass" and a second setting called "hold", the change from the first setting to the second setting being effected by a modification of the diameter of said deformable element.

One advantage is to make it possible to hold in place a cannula for a long time. This is particularly advantageous when the cannula device is used for an artificial lung application. Another advantage when a lumen is introduced into a cavity of the heart, for example, is to enable good stability and holding despite movements linked to the contraction of the heart.

According to one embodiment, the injection lumen comprises at the distal end thereof the deformable element which is meshed so as to enable the passage of a fluid between its meshes.

According to one embodiment, the deformable element is meshed and extensible so as to enable the passage of a fluid between its meshes.

One advantage is that the deformable element enables the passage of a fluid, to this end the meshes may be configured so as to enable a maximum flow rate.

According to one embodiment, the deformable element forms the distal orifice of the injection lumen at the distal end thereof so as to enable the passage of a fluid between its meshes.

According to one embodiment, the deformable element prolongs the distal orifice of the injection lumen at the distal end thereof so as to enable the passage of a fluid between its meshes.

According to one embodiment, the deformable element is extensible and retractable.

According to one embodiment the first setting of the deformable element is obtained by extension of said deformable element, the diameter of the deformable element then being below a first threshold, the second setting of the deformable element is obtained in the rest shape thereof, the diameter of the deformable element then being above a second threshold.

One advantage is to enable the introduction of the lumen under stress in order to relax the stress once the cannula device is in place. Consequently, the cannula device does not require stress to be maintained on the deformable element during its operation.

According to one embodiment, the deformable element is an element with "shape memory".

According to one embodiment, the deformable element is a Stent.

According to one embodiment, the deformable element comprises a rest shape forming a first means of holding the cannula device, one of the rest shapes being able to be one of the following:

A mushroom shape,
A plate shape,
A trumpet shape,
A balloon shape.

One advantage is to have available a shape making it possible to block the passage of the cannula in the orifice of the wall.

According to one embodiment, the deformable element prolongs the distal orifice of the injection lumen, said deformable element comprising a closed distal tip.

According to one embodiment, the closed distal tip performs a support function for a guiding device introduced into the injection lumen and exerting a bearing force on said distal tip being capable of bringing about the extension of the deformable element in the longitudinal direction prolonging the axis of the injection lumen.

According to one embodiment, the aspiration lumen and the injection lumen are coaxial, the aspiration lumen having a diameter greater than the diameter of the injection lumen. One advantage of this configuration is that the cannula device may be guided simply. The guiding of one lumen brings about the guiding of the second lumen.

According to one embodiment, the aspiration lumen enables the circulation of a fluid between the outer surface of the injection lumen and the inner surface of the aspiration lumen over at least a portion of the cannula device.

According to one embodiment, the junction between the aspiration lumen and the injection lumen is formed by a progressive reduction in the diameter of the aspiration lumen over at least a portion so as to form a second holding means holding the cannula device in a direction opposite to a force resulting from the holding of the second setting. According to one embodiment, the two lumens are stuck onto a circumferential portion of the outer surface of the injection lumen. According to another embodiment, they are formed jointly for example by moulding.

According to one embodiment, the junction between the aspiration lumen and the injection lumen forms a stop comprising an increase in the diameter of the cannula device forming a third holding means holding the cannula device in a direction opposite to a force resulting from the holding of the second setting.

According to one embodiment, the aspiration lumen comprises a plurality of orifices arranged on its periphery.

According to one embodiment, the cannula device comprises a guiding device cooperating with the tip of the injection lumen to cause an extension of the deformable element in the longitudinal direction prolonging the axis of the injection lumen.

Another object of the invention relates to an artificial lung comprising:
  a cannula device of the invention,
  a pump arranged to ensure the pumping of a predetermined flow rate of fluid, said aspiration lumen cooperating with an inlet of the pump via an interface tube,
  an oxygenator arranged to introduce a proportion of oxygen into a fluid, an inlet of the oxygenator cooperating with an outlet of the pump via a second interface tube,
    a heat exchanger arranged to inject oxygen supplied by the oxygenator at a set temperature into a volume of fluid injected into an injection lumen of the cannula device via a third interface tube, said exchanger being connected to the oxygenator and to the cannula device via a fourth interface tube.

According to one embodiment, at least one tube is covered with a layer of heparin.

According to one embodiment, the pump is arranged and configured to establish a pulsed flow of blood.

According to one embodiment, the oxygenator comprises a fibre coating.

According to one embodiment, the oxygenator comprises means for establishing a laminar flow of oxygen.

BRIEF DESCRIPTION OF THE FIGURES

Other characteristics and advantages of the invention will become clear on reading the detailed description that follows, with reference to the appended figures, which illustrate.

DETAILED DESCRIPTION OF EMBODIMENTS OF THE INVENTION

Cannula Device

The invention relates to a double lumen LA and LI cannula device comprising a meshed deformable element which is designated "Stent" and noted STN, arranged at the distal end of one of the lumens. A first lumen LI makes it possible to inject oxygenated blood into an organ, it is called injection lumen LI. The second lumen LA makes it possible to aspire blood low in oxygen which will be re-oxygenated in order to be reintroduced. The Stent STN is held at the distal end of the injection lumen LI. It notably performs a function of holding the lumen LI in the organ or the artery that is targeted. This function is vital given that the lumen LI has to be constantly held in an organ into which blood rich in oxygen is injected.

Different embodiments are described with regard to the figures. In order to better understand the figures, it should be noted that the cannula device 1 is intended to make blood circulate between a heart and an artificial lung. A first lumen LA is intended for the aspiration of blood to the artificial lung, a second lumen LI is intended to inject blood into the heart or an artery.

Lumens

"Double lumen" is taken to mean the presence of two hollow elements such as for example tubes. Each lumen comprises at least two orifices of which an orifice at each end. The orifices may be made either on the circumference of an end of a closed tube, or at the end of an open tube. The two orifice embodiment possibilities may also be combined.

The orifices make it possible to transport blood either to an organ or to a component of the artificial lung. The cannula device 1 comprises two lumens LI and LA, each thus performing a cannula function. The terms "lumen" or "cannula" will be used indiscriminately in the remainder of the description.

A lumen is an element such as a sheath comprising at least two orifices at each of the ends thereof. It may be made of a single part or may comprise several hollow cylindrical parts that prolong each other. If the lumen comprises different parts, each part is rigidly connected to the other parts so as to form an extending hollow one-piece element E1.

Figure 1:
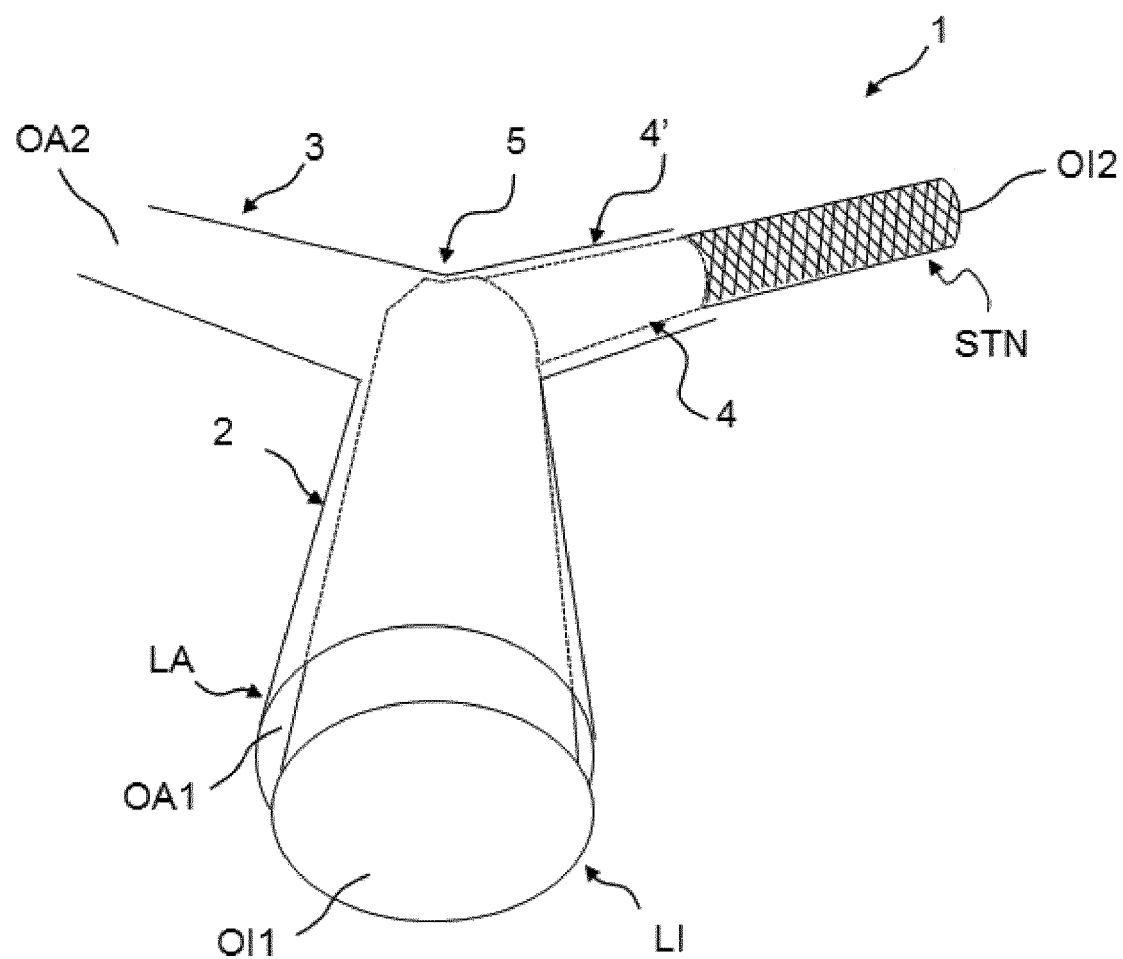
FIG. 1: a schematic representation of the double lumen cannula device according to a first embodiment of the invention.
Figure 2:
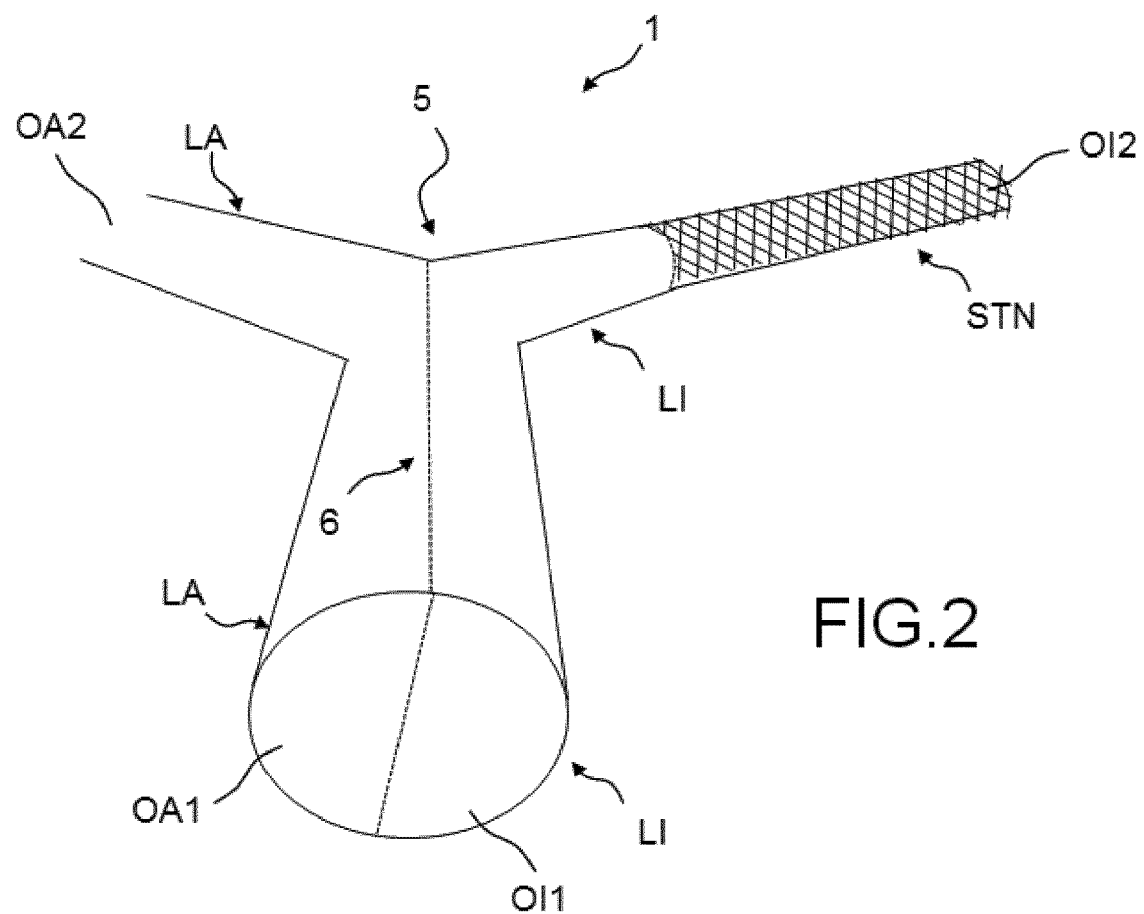
FIG. 2: a schematic representation of the double lumen cannula device according to a second embodiment of the invention.
Figure 3:
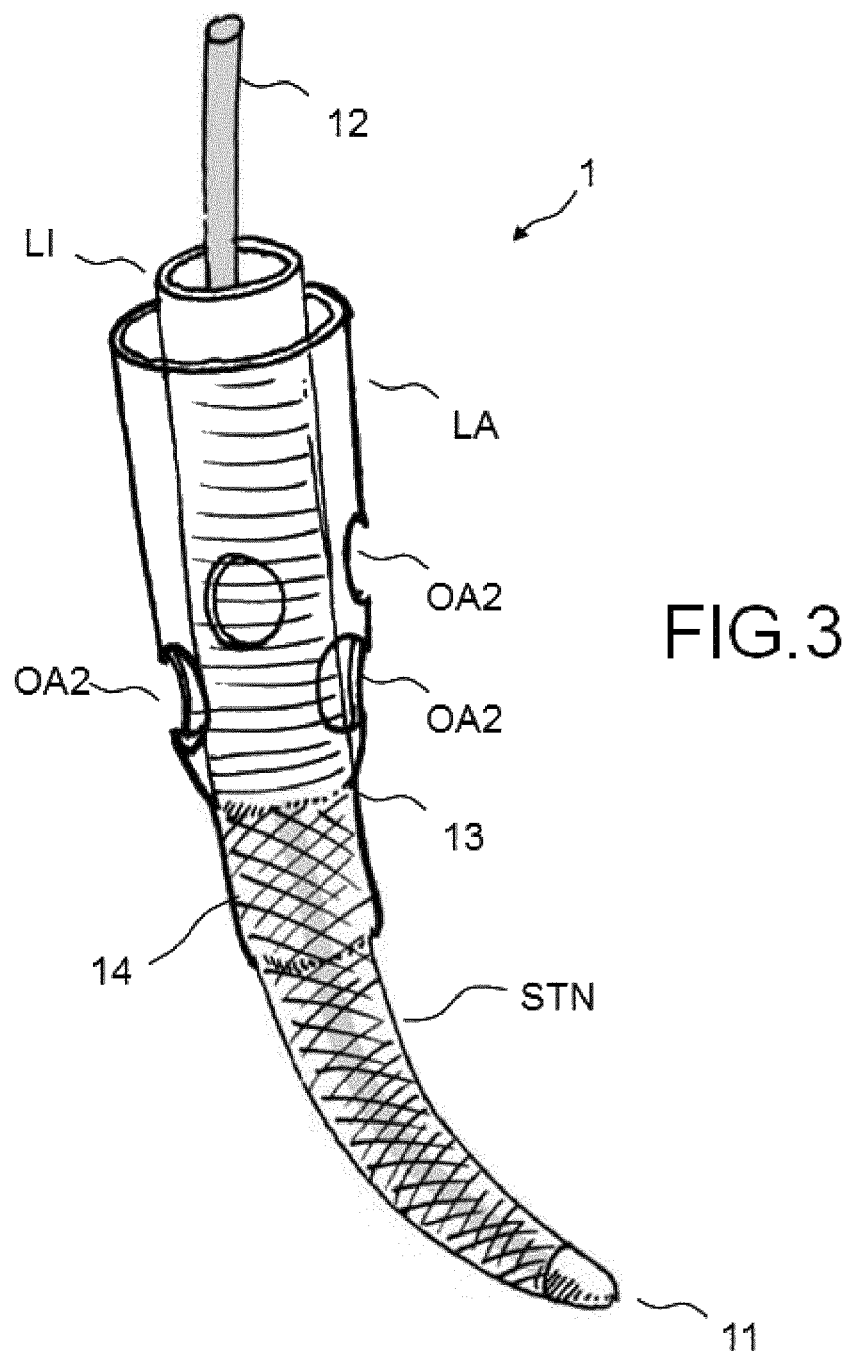
FIG. 3: a schematic representation of the double lumen cannula device according to a third embodiment of the invention.

According to one embodiment, the shape of a cannula device 1 comprising two lumens rigidly connected over a portion of said device may take a "lengthened Y-shape" in the case of FIG. 1 or 2. According to another embodiment, the lumens may be coaxial and not separate into a Y-shape as the embodiment of FIG. 3 illustrates.

The cannula device 1 comprises lumens having a certain suppleness and flexibility to enable their guiding into the body of a patient. The guiding may be ensured by one or more guiding device(s) which is/are introduced into at least one lumen of the device of the invention.

Orifices

Moreover, each lumen comprises orifices:
an orifice OI1 corresponds to the orifice of the proximal end of the injection lumen LI which cooperates with an ECMO type artificial lung device,
an orifice OI2 corresponds to the orifice of the distal end of the injection lumen LI which enables the injection of oxygenated blood into the heart or an artery,
an orifice OA1 corresponds to the orifice of the proximal end of the aspiration lumen LA which cooperates with an ECMO type artificial lung device,
an orifice OI2 corresponds to the orifice at the distal end of the aspiration lumen LA which enables the aspiration of blood low in oxygen.

Each lumen may comprise at one of the ends thereof one or more orifices.

Different double lumen cannula devices exist. FIGS. 1, 2 and 3 represent three embodiments of a double lumen cannula device of the invention. As regards the cooperation of the Stent STN with the end of the injection lumen LI, the embodiment of FIG. 3 may be combined with the embodiments of FIGS. 1 and 2.

Double Lumen Cannula Device: 1$^{st}$ Embodiment

The first embodiment represents a cannula device 1 comprising two lumens LI and LA which are concentric over a first portion 2 and diverge over a second portion 3 and 4 of the cannula device. According to one embodiment, the cannula device 1 separates into two separate lumens 3 and 4 from the common portion 2. Each lumen is conveyed into a desired region of an artery, a vein or an organ to inject therein or to withdraw therefrom a volume of blood.

According to an alternative embodiment, the body of a first lumen, for example the aspiration LA, may be divided into two parts so as to be prolonged over a part of the second lumen as is represented by part 4' of FIG. 1.

In this embodiment, the injection lumen LI is prolonged at the end thereof by a Stent STN which has the function of holding the lumen in an organ or an artery once the latter has been positioned to operate and to inject blood.

The Stent STN is arranged at the end of the injection lumen LI during the introduction of the cannula device 1. It may be, for example, placed under tension or compressed to be deformed and thereby to facilitate the introduction of the injection lumen LI into the desired cavity through an orifice.

Once arranged, the cannula device 1 is configured so that the Stent STN holds the injection lumen LI in a cavity such as an atrium or an artery.

The Stent STN may be, for example, placed under tension during the introduction of the cannula device 1 and relaxed when it is positioned for its operation.

Double Lumen Cannula Device: 2$^{nd}$ Embodiment

In this second embodiment, the injection LI and aspiration LA lumens are held fixed to each other over a common portion of the cannula device 1 of the invention. This embodiment makes it possible to have available two specific channels for each of the lumens LI and LA and to configure an independent flow for one or the other of the lumens.

A separation of the lumens 5 makes it possible to transport the injection lumen LI into a cavity for the injection of a volume of oxygenated blood and to transport the aspiration lumen LA for the withdrawal of a volume of blood low in oxygen.

The orifices OI1, OI2 and OA1 and OA2 are represented in FIG. 2 in a manner similar to FIG. 1.

At the distal ends of the lumens LI and LA, the lumen may comprise one or more orifice(s) according to the alternative embodiments. The orifices may be arranged on the longitudinal distal end of the lumen or instead arranged laterally on the circumference of a lumen.

As an example, the Stent represented in FIGS. 1 and 2 may cover a plurality of orifices, the longitudinal end of the lumen LI being closed.

Double Lumen Cannula Device: 3$^{rd}$ Embodiment

FIG. 3 represents a particularly advantageous embodiment. The lumens LI and LA are concentric over the entire length of the aspiration lumen LA. The aspiration lumen comprises an ending 13 making it possible to merge with the outer surface of the injection lumen. This ending may be obtained by manufacture and assembly of sheaths forming the lumens ensuring a sealing between the two lumens LI and LA.

In this embodiment, the injection lumen prolongs, in the continuity of the axis common to the two concentric lumens, a portion 14 covered by a Stent STN. The STN is advantageously fixed to the distal part of the injection lumen by stitching, bonding or instead by any method making it possible to fix a Stent STN to a sheath for cannula.

The cannula device 1 in this embodiment comprises at the distal end thereof a Stent STN which is closed at the end thereof by a tip 11. The Stent STN comprises orifices for the injection of blood rich in oxygen. Notably, when the Stent STN forms an extensible meshed fabric, the orifices are the meshes of the Stent STN.

In this embodiment, the aspiration lumen LA comprises a plurality of openings OA2 which make it possible to withdraw a volume of blood low in oxygen.

In this embodiment, it is understood that the end 11 makes it possible to form a bearing point for the guiding device 12 which is introduced into the cannula device 1 of the invention to transport it into the cavity in which it will operate with the artificial lung.

Figure 4:
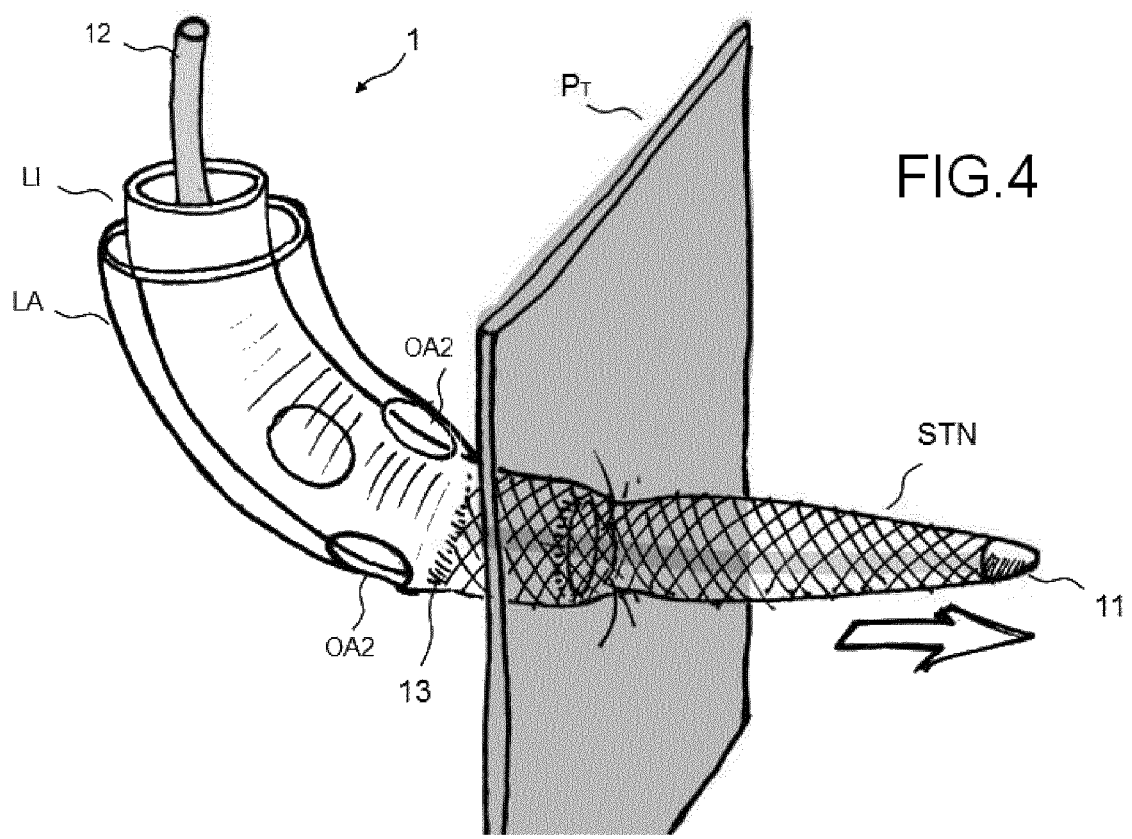
FIGS. 4 to 6: a representation of the introduction of a double lumen cannula device of the third embodiment of the invention.

FIG. 4 illustrates the introduction of the cannula device 1 into a wall such as a wall separating the atriums of the heart for the injection of a volume of oxygenated blood. According to one embodiment, the injection lumen LI is introduced into the left atrium OG of the heart via the transseptal wall $P_T$ which is represented in FIG. 4 by the annotation $P_T$.

The piercing of the transseptal wall may be carried out prior to the introduction of the cannula device of the invention.

Figure 5:
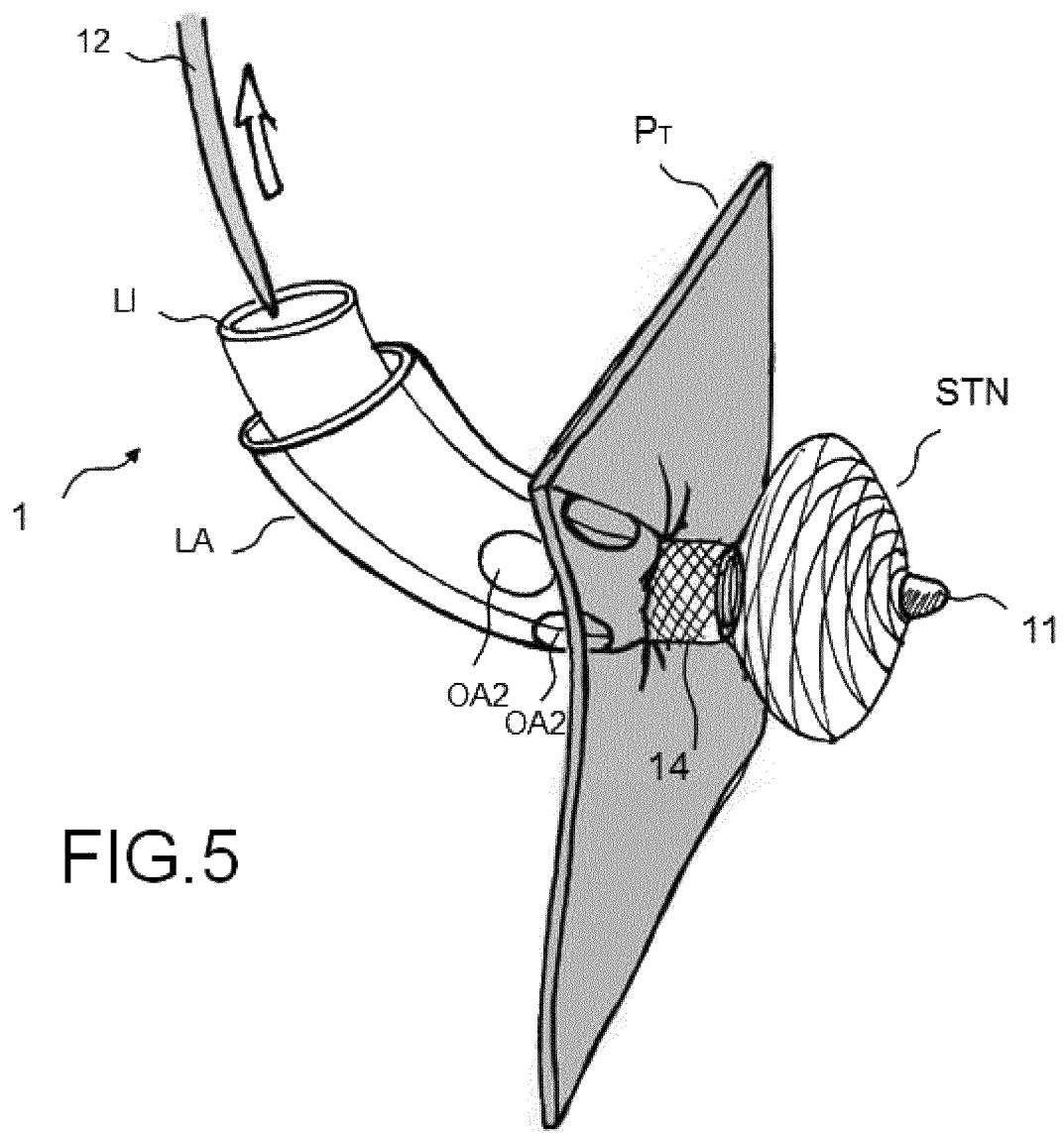

FIG. 5 illustrates, after the positioning of the injection lumen LI, the removal of the guiding device 12 and the deployment of the Stent STN in a hold position. In this embodiment, the Stent takes the volume, for example, of an ovoid or a mushroom enabling the injection lumen LI to be held in the left atrium OG. One advantage of such a cannula device 1 is that said device makes it possible to overcome movements induced by the beating of the heart and the left atrium which contracts and relaxes regularly and causes a force which tends to push the injection lumen LI back towards the orifice of the transseptal wall $P_T$.

In FIG. 5, the portion 14 of the injection lumen LI is covered with the Stent STN. On this portion the injection lumen LI and the Stent STN are rigidly connected and fixed thanks to an adhesive or a stitch for example. The Stent STN is prolonged over a portion which has changed shape due to the withdrawal of the guiding device 12. The shape of the Stent which is prolonged beyond the injection lumen has a greater volume than the diameter of the orifice of the wall $P_T$ once it has been deployed.

According to one embodiment, the Stent STN is introduced under tension thanks to the guiding device 12 which enables the Stent to be extended over its whole length during its introduction into the orifice of the wall $P_T$. When the guiding device 12 is removed, the Stent, which has a shape memory, recovers its initial volume, of ovoid or mushroom shape in the example of FIG. 5.

Other shapes of Stent may be envisaged from the moment where the diameter of the shape of the Stent in deployed position is greater than the diameter of the orifice formed in the transseptal wall.

Figure 6:
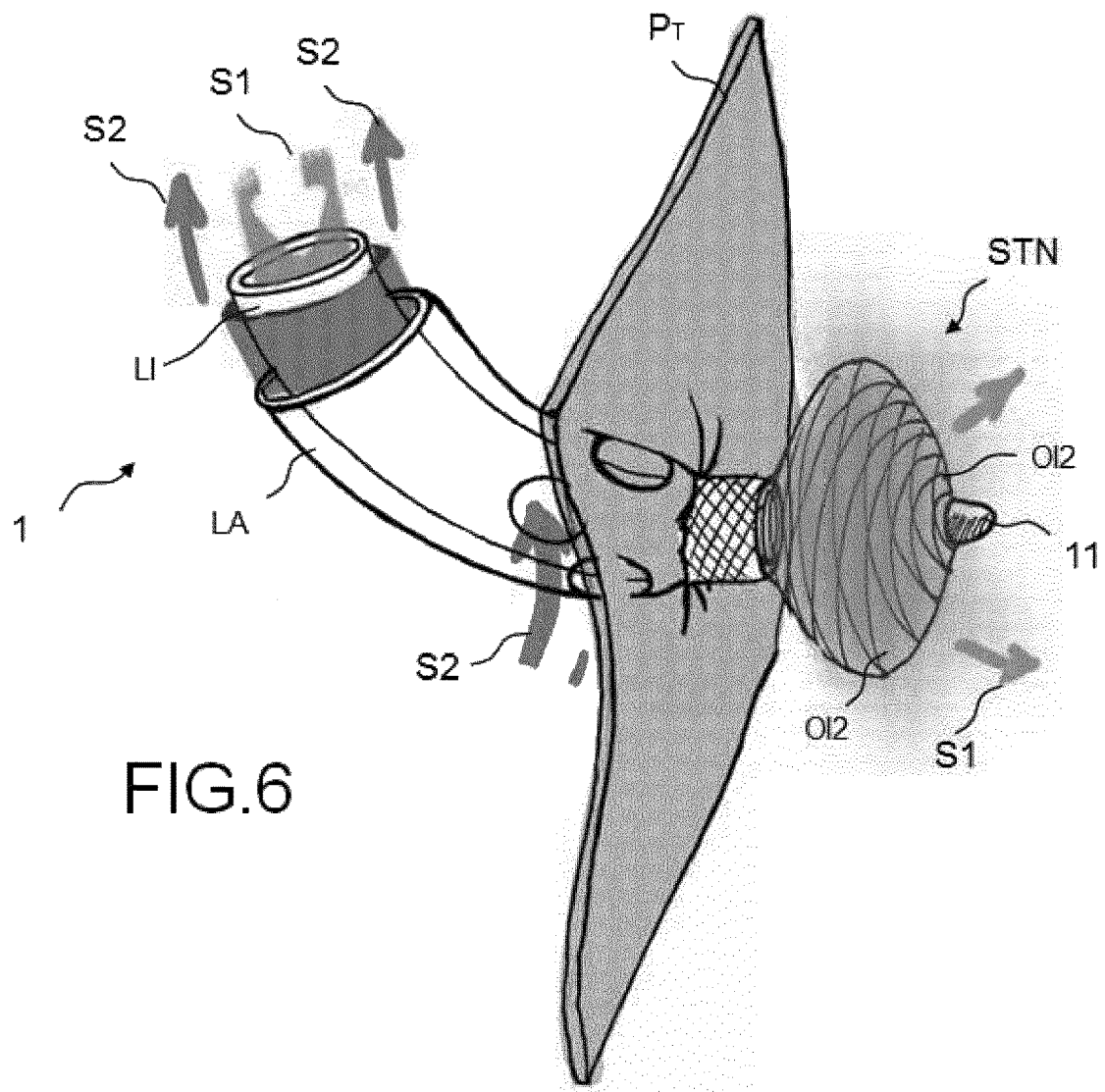

FIG. 6 represents an operating mode when the cannula device is arranged suitably, that is to say with the injection lumen LI in the left atrium OG. FIG. 6 makes it possible to represent the volume of oxygenated blood S1 which is introduced into the left atrium OG, that is to say beyond the transseptal wall $P_T$ notably through the distal orifice OI2 of the injection lumen LI and orifices of the Stent STN forming open meshes in deployment position.

The flow S2 sucked up through the orifices OA2 and rising via the lumen LA up to the artificial lung is represented.

Stent STN

"Stent" is taken to mean a deformable element preferentially by extension and meshed. Such an element is comparable to a spring, which can deform then recover its rest shape.

In one embodiment, the Stent STN has shape memory. Shape memory is taken to mean an element which can be compressed or stretched when a pressure/tension is applied thereto. During its relaxation, the Stent STN may take a given/fixed shape such as a trumpet, a mushroom, etc.

One advantage is when it is wished to remove the cannula device, a guiding device 12 may be reintroduced into the injection lumen LI. When it is reintroduced, it may exert on the distal tip 11 making it possible to form a bearing surface, the guiding device enabling the elongation of the Stent STN. The Stent thereby lengthened may be removed via the orifice of the transseptal wall $P_T$.

Thus, during its introduction into the left atrium OG by piercing of a hole in the auricular transseptal wall, the Stent STN is:
  either held extended by extension of the meshed tissue as is represented in the examples of FIGS. 5 and 6,
  or held squeezed or compressed, so as to hug the shape of the cannula device 1. Such a compression makes it possible to introduce the cannula device 1 rigidly connected to the Stent STN through the hole made in the wall.

In the latter case, the Stent recovers its initial shape, for example by shape memory, the diameter of which then becomes greater than the orifice of the pierced wall.

According to one embodiment, the Stent STN is metallic, for example made of stainless steel or instead made of a cobalt-chromium or platinum-chrome alloy or instead nitinol.

According to another embodiment, the Stent STN is manufactured from an elastomeric material or instead a composite material.

According to one embodiment, the Stent STN has a meshed surface.

According to the embodiment, the Stent STN is held at the distal end of the injection lumen LI over a portion of the outer surface thereof such as the portion 14 of FIGS. 3 and 5. According to an alternative embodiment, the Stent STN may be held over a portion of the inner surface of the injection lumen LI.

In these embodiments, the Stent STN prolongs the injection lumen LI beyond the distal end of said lumen LI. In this case, the Stent STN is not superimposed on the final portion of the injection lumen LI.

Figures 7A, 7B, 7C:
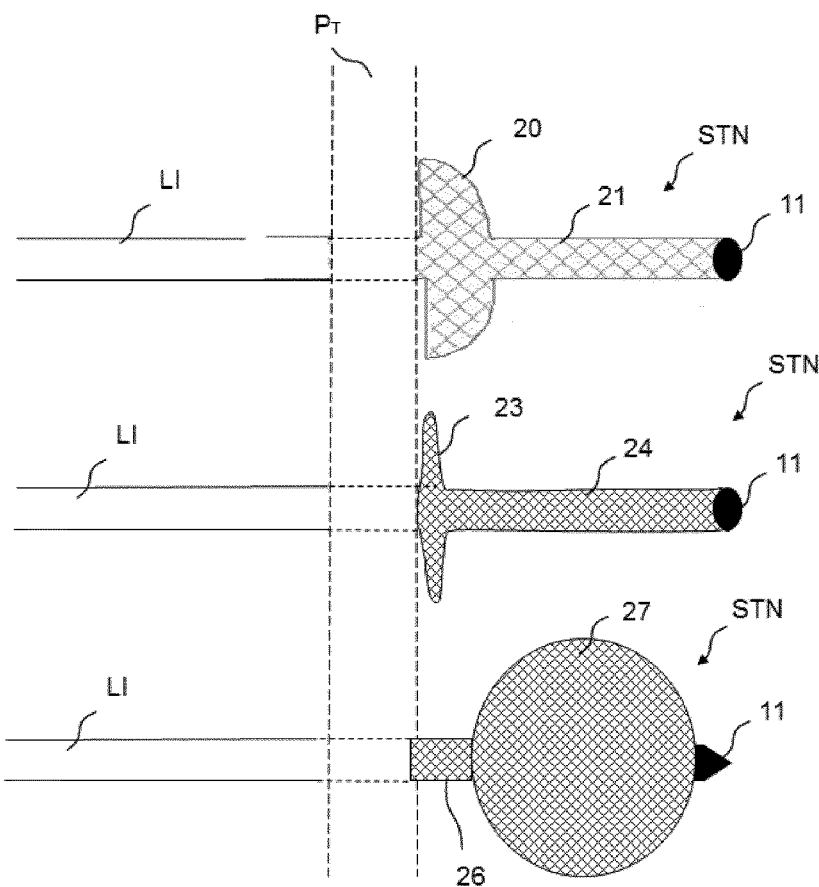
FIGS. 7A to 7C: different embodiments of a Stent arranged at the end of an injection lumen of the cannula device of the invention.

FIG. 7A represents an embodiment of a Stent STN of the invention. It comprises a part 20 with shape memory having a mushroom shape and making it possible to retain the injection lumen LI in a cavity once said lumen has been positioned. The Stent STN comprises a part 21 which prolongs the part 20. Over this extension, the lumen LI may also be prolonged. A distal tip 22 makes it possible to close the lumen LI and to serve as guiding element when the guiding device 12 of the cannula device 1 is actuated for the positioning of the lumen LI. When the lumen LI also prolongs the portion comprising the Stent STN, the latter may advantageously comprise orifices enabling the passage of oxygenated blood through said orifices then through the meshes of the Stent STN.

According to the embodiment, the diameter of the Stent STN increases over a portion of the Stent STN only according to the shape memory formed. Such a shape enables the Stent STN and thus the injection lumen LI to remain substantially fixed in the left atrium OG. Indeed, since the diameter of the Stent STN is greater than that of the hole formed in the transseptal wall, the Stent STN remains stuck against the wall separating the septum from the left atrium OG, preventing the cannula device 1 from moving and withdrawing through the orifice of the transseptal wall.

FIG. 7B represents an alternative embodiment of FIG. 7A in which the shape of the Stent with shape memory takes the shape of a plate or of a "trumpet", the diameter of which is greater than the diameter of the orifice of the transseptal wall $P_T$.

In the same way as for the embodiment represented in FIG. 7A, this shape of Stent STN over a portion of said Stent STN makes it possible to fix the cannula device 1 in a cavity of the heart while preventing it from moving despite contraction and relaxation movements of the heart.

FIG. 7C represents another embodiment substantially similar to the embodiments of FIGS. 5 and 6. In this case, the injection lumen may be prolonged over the portion 26. The portion 27 not fixed to the lumen LI, either because it is not prolonged in this portion, or because it is not fixed to the lumen which is prolonged, takes a balloon shape when the guiding device 12 is removed.

The Stent STN must be sufficiently rigidly connected to the cannula device 1 such that when the heart of a patient is in movement, the Stent STN does not risk remaining in the left atrium OG while the cannula device 1 is ejected from the left atrium through the orifice of the transseptal wall. Thus, the fixation of the Stent STN on the injection lumen is carried out so as to withstand a force of several Newtons.

Material

According to one embodiment, the material used for the manufacture of the lumens of the cannula device is semi-rigid thermosensitive PVC.

ECMO System

Figure 8:
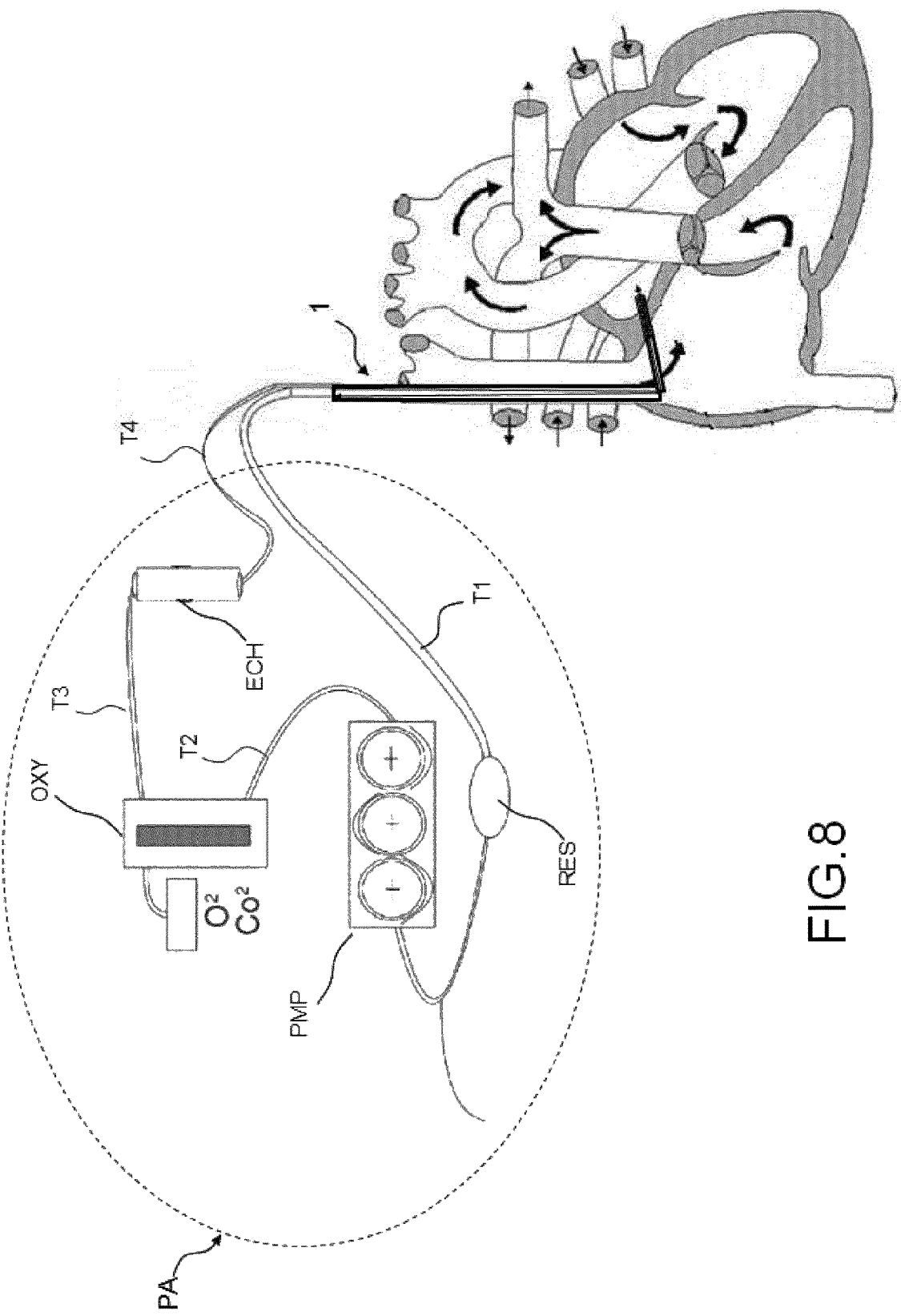
FIGS. 8 and 10: an extracorporeal membrane oxygenation (ECMO) system connected to a heart through the cannula device according to one of the embodiments of the invention.
Figure 9:
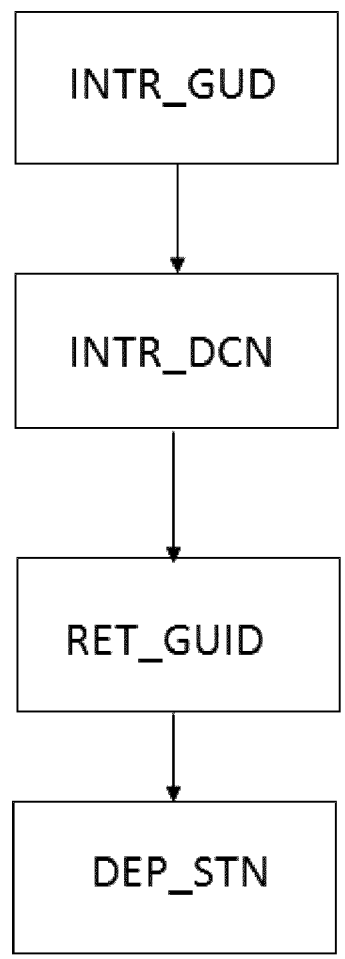
FIG. 9: a block diagram illustrating the steps of putting in place the cannula device of the invention in a region of the heart
Figure 10:
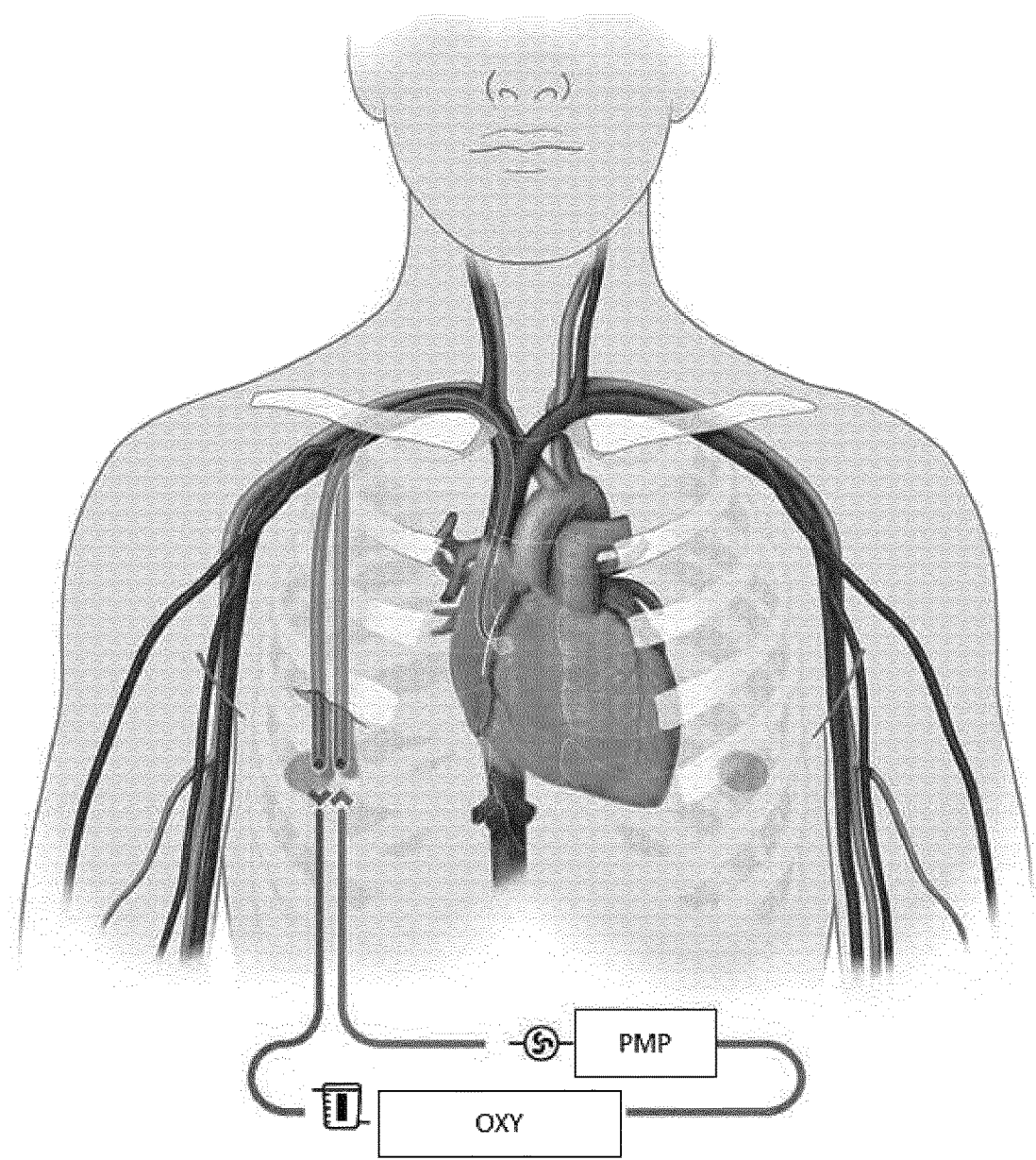
Figure 11:
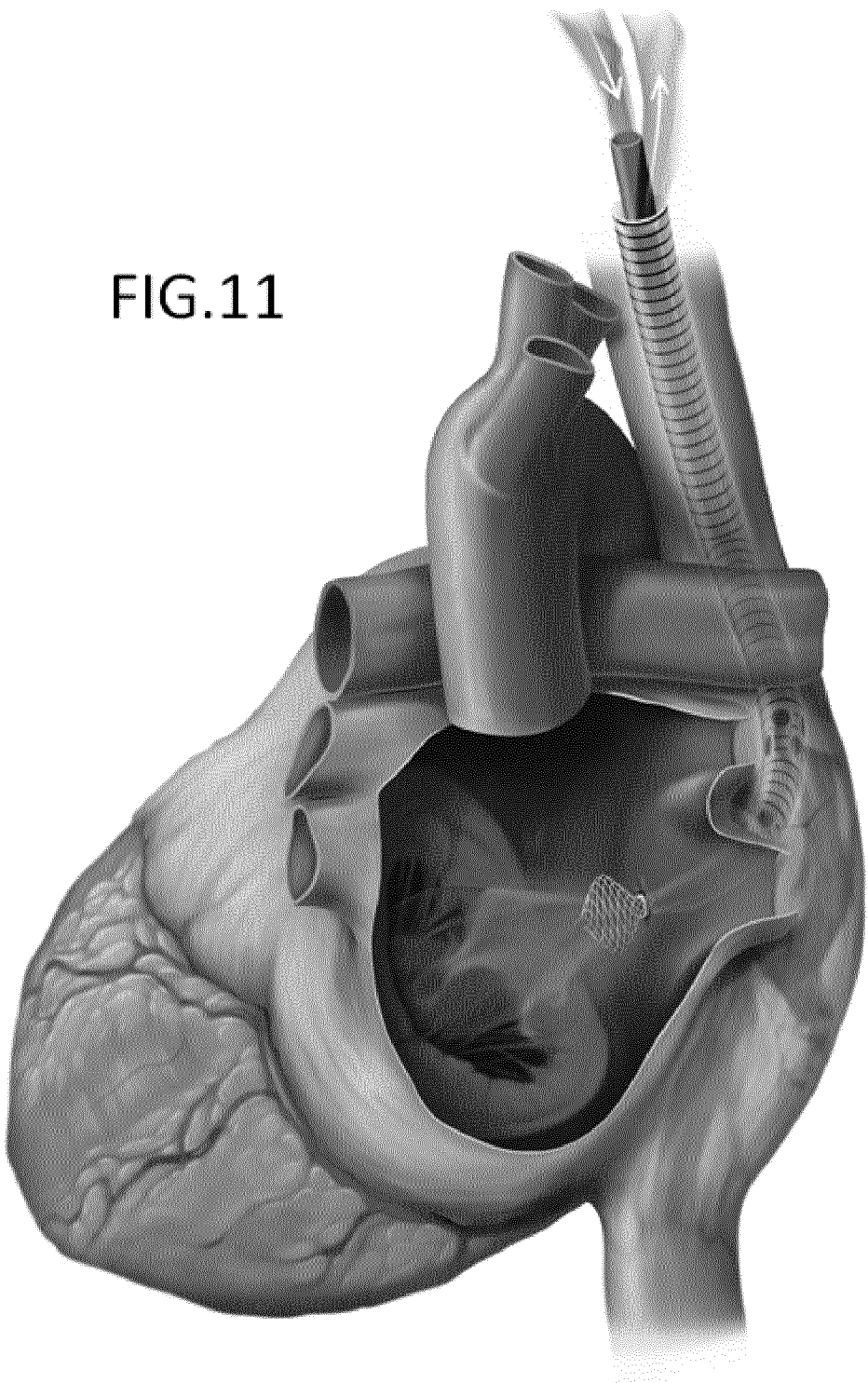
FIG. 11: a three-dimensional representation of the cannula device of the invention when it is introduced into the heart
Figure 12:
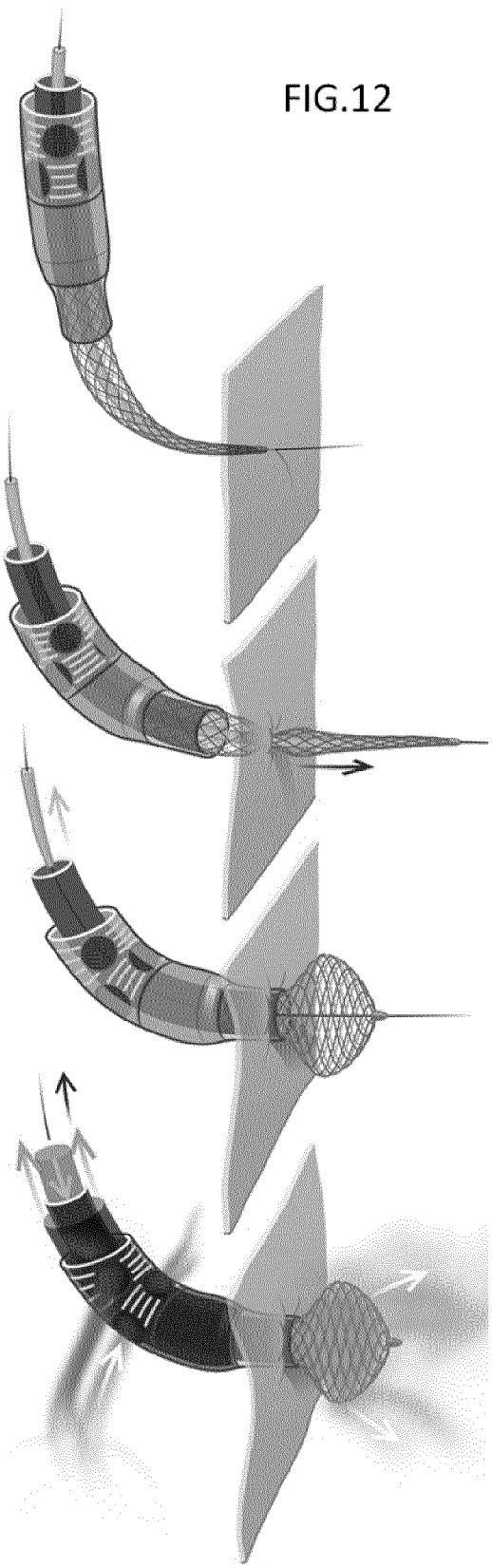
FIG. 12: the different steps of introduction of the cannula device into an orifice of a transseptal wall.

With reference to FIG. 8, the ECMO system comprises:
a cannula device 1,
a pump PMP,
an oxygenator OXY,
a heat exchanger ECH,
four tubes: T1, T2, T3 and T4.

Putting the Cannula Device in Place and Operation

According to one embodiment, the cannula device 1 is introduced into a region of the heart through the superior vena cava. According to another embodiment, the cannula device 1 is introduced into a region of the heart through the inferior vena cava.

According to the embodiment, the cannula device 1 comprises two lumens LI and LA which are independent while being rigidly connected to each other over a portion of the cannula device 1 such that they can receive, in parallel, different fluids moving at different flow rates.

Thus, the aspiration lumen of the cannula device 1 withdraws a volume of blood low in oxygen and rich in carbon dioxide at a fixed flow rate. The blood low in oxygen comes from the right atrium OD of the heart into which emerges the orifice OA2 of the aspiration lumen LA. The blood coming from the right atrium OD is next transported to an extra-corporeal membrane oxygenation ECMO system through the orifice OA1 of the aspiration lumen LA. Indeed, theoretically, the right atrium OD collects the blood that has passed through the whole body and sends it to the right ventricle VD so that it is ejected into the lungs to be oxygenated therein. According to the invention, before the blood low in oxygen contained in the right atrium OD is sent to the right ventricle, the blood is pumped to undergo oxygenation by the ECMO system.

The injection lumen LI of the cannula device 1 receives blood rich in oxygen at a set flow rate. The enrichment of the blood with oxygen results from treatment by the ECMO system which carries out oxygenation of the blood coming from the aspiration lumen LA. Blood rich in oxygen is introduced into the injection lumen LI of the cannula device 1 through the orifice LI1 then passes along the lumen LI up to the orifice LI2 emerging into the cavity of the left atrium OG. Indeed, theoretically, the left atrium OG has the role of collecting blood which has passed through the lungs to oxygenate it then to transport it to the left ventricle VG which ejects the oxygenated blood into the whole of the body.

Reservoir

According to one embodiment, the ECMO system comprises a venous reservoir RES. The function of the latter is to regulate the flow of blood treated by the artificial lung. The aspiration lumen of the cannula device 1 withdraws a volume of blood which is transported to the venous reservoir. In order to carry out drainage of the blood coming from the right atrium OD of the heart. According to one embodiment, this step is carried out before the pumping step explained hereafter.

Pump PMP

Said pump PMP ensures two roles: pumping of blood low in oxygen and rich in carbon dioxide coming from the aspiration lumen LA of the cannula device 1 and injection of oxygenated blood into the injection lumen LI of the cannula device 1.

The pump PMP is configured to pump blood low in oxygen at a flow rate suitable to the pumping needs of the heart. The flow rate must enable efficient decarboxylation carried out from the carbon dioxide contained in blood low in oxygen.

The pump PMP is also configured so that blood injected into the injection lumen LI is at a physiological flow rate, that is to say similar to that of a "natural" lung.

According to an exemplary embodiment, the pump PMP is of "centrifugal" type. A centrifugal pump PMP uses the rotational movement of a wheel inserted into the pump PMP. The wheel, turning at a high speed, displaces fluid by centrifugal effect and increases its pressure. Thus, the displacement and the flow rate of fluid may be set and controlled.

According to one embodiment, the pump PMP is a "roller" pump, also known as a "peristaltic" pump. A roller pump PMP is constituted of a head supporting a flexible pipe containing the fluid as well as a rotor comprising rollers. The rollers deform and seal the pipe during rotation which has the consequence of driving the displacement of the fluid found between two rollers. Thus, the displacement and flow rate of the fluid may be set and controlled.

According to one embodiment, the pump PMP generates a pulsed flow. Indeed, pulsed flow is more physiological, and makes it possible to preserve human cells during their passage in the oxygenator OXY.

According to one embodiment, the pump PMP is miniaturised so as to minimise the size of the ECMO system and thereby enable a patient to use it for a long time.

According to one embodiment, the pump PMP is biocompatible such that an artificial lung can be introduced and accepted by a human body.

Oxygenator OXY

The oxygenator OXY comprises a membrane which artificially reproduces the function of the alveolar-capillary membrane. This membrane makes it possible to ensure gaseous exchanges in order to oxygenate the blood and to eliminate the carbon dioxide contained in the blood by decarboxylation. The oxygenator OXY is connected to the pump PMP from which it receives blood low in oxygen and rich in carbon dioxide at a fixed flow rate.

According to one embodiment, the membrane of the oxygenator OXY is flat. Oxygenators OX with flat membranes comprise membranes made of silicone or membranes assembled in layers.

According to one embodiment, the membrane of the oxygenator OXY is tubular. These types of oxygenators OX are composed of composite hollow fibres, for example non-porous polymethylpentenes.

According to one embodiment, the fibres may comprise a coating offering less resistance to flow and favouring laminar flow.

According to one embodiment, endothelial cells are disseminated in the oxygenator to offer a bio-oxygenator. The pulsatile flow of the pump favours the growth of endothelial cells.

According to one embodiment, micro-fluids may reproduce the capillary vessels of the lungs to facilitate endothelialisation.

According to one embodiment, the oxygenator OXY is miniaturised so as to minimise the size of the ECMO system and thereby allow a patient to use it for a long time.

Heat Exchanger ECH

The heat exchanger ECH receives oxygenated blood from the oxygenator OXY in order to reheat it. Indeed, the blood passes through a system making it possible to transfer the thermal energy from a fluid such as water to the blood, without mixing the two fluids. The heat flux passes through the exchange surface which separates the oxygenated blood and the water. The heat exchanger ECH sets the temperature of the blood in order that it is comprised in the temperature interval of blood circulating in the body of a patient.

According to one embodiment the heat exchanger ECH is connected to a venous reservoir so as to reheat the blood after its drainage, the steps of pumping then of oxygenation are then carried out thereafter.

The orifice OI1 on the proximal end of the injection lumen LI of the cannula device 1 is connected to the heat exchanger ECH such that it receives the heated oxygenated blood. The oxygenated and heated blood passes along the injection lumen LI up to the orifice OI2 of the distal end thereof, longitudinal and/or circumferential.

Alternatively, according to another embodiment, the heating may come from the oxygenator itself. In this case, it advantageously comprises resistances provided for this purpose.

Tubes T1, T2, T3, T4

The pump PMP, the oxygenator OXY and the heat exchanger ECH and the cannula device 1 are connected together through four tubes T1, T2, T3 and T4. These tubes T1, T2, T3, T4 are intended to make oxygenated blood pass or not between the different elements enabling its treatment.

Thus, the tube T1 makes it possible to connect the orifice OA1 of the aspiration lumen of the cannula device 1 to the pump PMP. The tube T2 makes it possible to connect the pump PMP to the oxygenator OXY. The tube T3 makes it possible to connect the oxygenator OXY to the heat exchanger ECH and the tube T4 makes it possible to connect the heat exchanger ECH to the orifice OA1 of the injection lumen of the cannula device 1.

According to one embodiment, the tubes T1, T2, T3, T4 are dimensioned to be as short as possible so as to minimise the size. Thus, the length of the tubes T1, T2, T3, T4 is preferentially reduced to a minimum length to reduce the size of the device. In addition, the diameter of said tubes T1, T2, T3, T4 is chosen so as to enable blood to be displaced while minimising the risks of haemolysis and coagulation. Thus, the diameter of the tubes T1, T2, T3, T4 is adjusted according to known flow rates permitting the circulation of blood in the body.

According to one embodiment, the tubes T1, T2, T3, T4 have a heparin coating, an anticoagulant that thereby makes it possible to avoid the formation of blood clots inside the tubes T1, T2, T3, T4.

Method

FIG. 4 represents the steps of putting in place the cannula device 1 in a cavity of the heart, the left atrium.

According to a first step, INT_GUD, a piercing guide is introduced into the superior vena cava, said piercing guide being surmounted by a needle. Said piercing guide passes along the superior vena cava until it reaches the right atrium OD. The needle of the piercing guide is then oriented towards the auricular transseptal wall, on the side of the right atrium, in order to produce thereon an orifice. The orifice enables the right atrium OD and the left atrium OG to communicate to prepare for the introduction of the injection lumen LI.

According to one embodiment, the piercing of the orifice is carried out using a Rashkind manoeuvre.

According to one embodiment, the piercing of the orifice is controlled by radiography or any other imaging system such as an ultrasound device, an ultrasound machine or a scanner.

The dimensions of the needle are chosen so as to minimise the diameter of the orifice made in the wall while enabling the introduction of the cannula device 1, notably the injection lumen into the orifice.

The method of the invention may be carried out from the step INT_DCN, the piercing step being able to be carried out beforehand or jointly with the introduction of the cannula device 1. In other words, the piercing step is an optional step of the method of the invention.

According to a second step, INTR_DCN, the cannula device 1 is introduced into the superior vena cava up to the left atrium OG by means of a guiding device 12. This step is illustrated in FIG. 4. The guiding device 12 is introduced inside the injection lumen LI of said cannula device 1 and bears on a distal tip 11 to carry along said lumen LI. The guiding device 12 holds, in this example, the Stent STN in extended position, its diameter then being maintained as small as possible so that it can penetrate into the orifice of the transseptal wall. The injection lumen LI is introduced up to a stop 13 which forms the circumferential junction of the aspiration lumen LA with the injection lumen LI. Advantageously, the stop is formed by a progressive increase in diameter over a portion of the cannula device 1 making it possible to hold in place said cannula device 1 in the orifice. In an alternative embodiment, the increase in diameter at the circumferential junction 13 may be sudden so as to form a stop preventing the aspiration lumen LA from penetrating into the orifice of the transseptal wall. One advantage is to create a holding force in the direction opposite to the force resulting from the holding caused by the Stent STN in deployed position in accordance with the deployment step DEP_STN described hereafter.

Once the injection lumen has been positioned, as is represented in FIG. 5, a step of removal of the guide may be started.

According to a third step, RET_GUID, the guiding device 12 is removed. Since the Stent STN is no longer held on the distal end in extension position, it recovers its initial shape through shape memory. The Stent STN takes a shape, the diameter of which is greater than the diameter of the orifice. This step of deployment of the Stent STN is noted DEP_STN. This step results in this embodiment from the removal of the guiding device 12. It is thus carried out at the same time as the step of removal RET_GUID. According to one embodiment, the Stent STN takes several seconds to recover its shape memory, according to another example, the Stent STN deploys without delay following the removal of the guiding device 12.

Thus the cannula device 1 is held fixed on the one hand by the stop 13 and on the other hand by the Stent STN acting as a blocking means.

According to another embodiment, the deployment of the Stent STN is carried out by another device introduced into the injection lumen.

When the injection lumen is positioned and held in the left atrium, the aspiration lumen may withdraw a volume of blood in the right atrium thanks to at least one orifice OA2 on its circumference.

The invention claimed is:

1. A cannula device for the circulation of a blood in an artificial lung, the cannula device comprising:
an aspiration lumen comprising at least one orifice configured to aspirate a volume of blood low in oxygen,
an injection lumen comprising at least one orifice configured to inject a volume of oxygenated blood,
wherein the injection lumen and the aspiration lumen are held rigidly connected over at least a portion of their length, said injection and aspiration lumens being sealed in relation to each other, wherein the injection lumen being the only lumen of the cannula device which comprises at a distal end thereof a deformable element which is meshed so as to enable a passage of blood between its meshes, said deformable element being held over a portion of the distal end thereof, said deformable element comprising a first setting and a second setting, a change from the first setting to the second setting being effected by a modification of a diameter of said deformable element.

2. The cannula device according to claim 1, wherein the deformable element is meshed, extensible and retractable.

3. The cannula device according to claim 1, wherein:
the first setting of the deformable element is obtained by extension of said deformable element, the diameter of the deformable element then being below a first threshold,
the second setting of the deformable element is obtained when the deformable element is in rest shape, the diameter of the deformable element then being above a second threshold.

4. The cannula device according to claim 1, wherein the deformable element is an element with shape memory.

5. The cannula device according to claim 1, wherein the deformable element is a stent.

6. The cannula device according to claim 1, wherein the deformable element comprises a rest shape forming a first device configured to hold the cannula device, the rest shape being able to be one of the following:
a mushroom shape,
a plate shape,
a trumpet shape,
a balloon shape.

7. The cannula device according to claim 1, wherein the deformable element prolongs the distal orifice of the injection lumen, said deformable element comprising a closed distal tip.

8. The cannula device according to claim 7, wherein the closed distal tip performs a support function for a guiding device introduced into the injection lumen and exerting a bearing force on said distal tip and being capable of leading to the extension of the deformable element in a longitudinal direction prolonging an axis of the injection lumen.

9. The cannula device according to claim 1, wherein the aspiration lumen and the injection lumen are coaxial, the aspiration lumen having a diameter greater than the diameter of the injection lumen.

10. The cannula device according to claim 9, wherein the aspiration lumen enables a circulation of blood between an outer surface of the injection lumen and an inner surface of the aspiration lumen over at least a portion of the cannula device.

11. The cannula device according to claim 10, wherein a junction between the aspiration lumen and the injection lumen is formed by a progressive reduction in the diameter of the aspiration lumen over at least a portion so as to form a second holding device configured to hold the cannula device in a direction opposite to a force resulting from the holding of the second setting.

12. The cannula device according to claim 10, wherein a junction between the aspiration lumen and the injection lumen forms a stop comprising an increase in the diameter of the cannula device forming a third holding device configured to hold the cannula device in a direction opposite to a force resulting from the holding of the second setting.

13. The cannula device according to claim 1, wherein the aspiration lumen comprises a plurality of orifices arranged on a periphery thereof.

14. The cannula device according to claim 1, further comprising a guiding device cooperating with a tip of the injection lumen to cause an extension of the deformable element in a longitudinal direction prolonging an axis of the injection lumen.

15. An artificial lung comprising:
a cannula device for the circulation of a fluid in the artificial lung, the cannula device comprising:
an aspiration lumen comprising at least one orifice configured to aspirate a volume of the fluid,
an injection lumen comprising at least one orifice configured to inject a volume of the fluid,
wherein the injection lumen and the aspiration lumen are held rigidly connected over at least a portion of their length, said injection and aspiration lumens being sealed in relation to each other, wherein the injection lumen comprises at a distal end thereof a deformable element which is meshed so as to enable a passage of a fluid between its meshes, said deformable element being held over a portion of the distal end thereof, said deformable element comprising a first setting and a second setting, a change from the first setting to the second setting being effected by a modification of a diameter of said deformable element,
a pump arranged to ensure pumping of a predetermined flow rate of fluid, said aspiration lumen cooperating with an inlet of the pump via an interface tube,
an oxygenator arranged to introduce a proportion of oxygen into a fluid, an inlet of the oxygenator cooperating with an outlet of the pump via a second interface tube,
a heat exchanger arranged to inject oxygen supplied by the oxygenator at a set temperature into a volume of fluid injected into an injection lumen of the cannula device via a third interface tube, said exchanger being connected to the oxygenator and to the cannula device via a fourth interface tube.

16. The artificial lung according to claim 15, wherein at least one tube is covered with a layer of heparin.

17. The artificial lung according to claim 15, wherein the pump is arranged and configured to establish a pulsed flow of blood.

18. The artificial lung according to claim 15, wherein the oxygenator comprises a fibre coating.

19. The artificial lung according to claim 15, wherein the oxygenator comprises a system configured to establish a laminar flow of oxygen.

* * * * *